(12) United States Patent
Kim et al.

(10) Patent No.: US 11,974,855 B2
(45) Date of Patent: May 7, 2024

(54) METHOD FOR DETECTING NOISE LEVELS IN ECG SIGNALS USING A CHANNEL CONSISTENCY THRESHOLD

(71) Applicant: West Affum Holdings Corp., Grand Cayman (KY)

(72) Inventors: Jaeho Kim, Redmond, WA (US); Joseph L. Sullivan, Kirkland, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 402 days.

(21) Appl. No.: 17/221,647

(22) Filed: Apr. 2, 2021

(65) Prior Publication Data

US 2022/0133208 A1 May 5, 2022

Related U.S. Application Data

(60) Provisional application No. 63/109,761, filed on Nov. 4, 2020.

(51) Int. Cl.
| | |
|---|---|
| A61B 5/366 | (2021.01) |
| A61B 5/00 | (2006.01) |
| A61B 5/024 | (2006.01) |
| A61B 5/282 | (2021.01) |
| A61N 1/39 | (2006.01) |

(52) U.S. Cl.
CPC .............. *A61B 5/366* (2021.01); *A61B 5/024* (2013.01); *A61B 5/282* (2021.01); *A61B 5/7203* (2013.01); *A61N 1/3904* (2017.08)

(58) Field of Classification Search
None
See application file for complete search history.

(56) References Cited

U.S. PATENT DOCUMENTS

| | | |
|---|---|---|
| 3,724,455 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |

(Continued)

FOREIGN PATENT DOCUMENTS

WO 1998039061 A2 9/1998

OTHER PUBLICATIONS

Pagan-Carlo, et al., "Encircling Overlapping Multipulse Shock Waveforms for Transthoracic Defibrillation," JACC Journals, Dec. 1998, vol. 32 Issue 7, p. 2065-2071.

(Continued)

*Primary Examiner* — Kennedy Schaetzle
(74) *Attorney, Agent, or Firm* — Columbia IP Law

(57) ABSTRACT

In one embodiment, a method to detect noise levels in electrocardiogram (ECG) signals. The method includes connecting to at least three sensing electrodes and obtaining a signal from each of the at least three sensing electrodes. The method also includes defining at least three channels between the at least three electrodes and obtaining heart data for a predetermined time period from the at least three channels wherein the heart data includes heart rate and QRS width. The method further includes comparing the heart data of each of the at least three channels to a consistency threshold.

20 Claims, 9 Drawing Sheets

(56) References Cited

U.S. PATENT DOCUMENTS

| | | | |
|---|---|---|---|
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,032,072 A * | 2/2000 | Greenwald | A61B 5/291 600/397 |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 10/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan | |
| 11,471,693 B1 * | 10/2022 | Sullivan | A61B 5/6805 |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2007/0239220 A1 * | 10/2007 | Greenhut | A61B 5/7221 607/32 |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0119733 A1 * | 4/2015 | Grubis | A61B 5/02055 600/509 |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2022/0409118 A1 * | 12/2022 | Sullivan | A61B 5/282 |
| 2023/0084533 A1 * | 3/2023 | Liu | A61B 5/256 600/544 |

OTHER PUBLICATIONS

The LifeVest Network/Patient Data Management System, Zoll, 2015, 2000503 Rev A.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

* cited by examiner

METHOD FOR DETECTING NOISE LEVELS IN ECG SIGNALS USING A CHANNEL CONSISTENCY THRESHOLD

CROSS-REFERENCE TO RELATED PATENT APPLICATIONS

This patent application claims benefit of U.S. Provisional Patent Application No. 63/109,761 filed Nov. 4, 2020, and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death very quickly, e.g., within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest and continuously monitors the patient's intracardiac electrogram (IEGM). If certain types of heart arrhythmias are detected, then the ICD delivers an electric shock through the heart.

As a further precaution, people who have been identified to have an increased risk of SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or another garment that the patient wears. The WCD system further includes electronic components, such as a defibrillator and electrodes, coupled to the harness, vest, or another garment. When the patient wears the WCD system, the electrodes may electrically contact the patient's skin and aid in sensing the patient's electrocardiogram (ECG). If a shockable heart arrhythmia (e.g., ventricular fibrillation or VF) is detected from the ECG, then the defibrillator delivers an appropriate electric shock through the patient's body through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs and methods.

In one embodiment, a method to detect noise levels in electrocardiogram (ECG) signals is described. The method includes connecting to at least three sensing electrodes and obtaining a signal from each of the at least three sensing electrodes. The method also includes defining at least three channels between the at least three electrodes and obtaining heart data for a predetermined time period from the at least three channels wherein the heart data includes heart rate and QRS width. The method further includes comparing the heart data of each of the at least three channels to a consistency threshold.

In some embodiments, the method may include determining when at least one of the at least three channels satisfies the consistency threshold and performing a rhythm analysis using the at least one channel that satisfies the consistency threshold. In some embodiments, the consistency threshold is measured as a predetermined percentage of the measurements being within a predefined value range. In some instances, the predefined value range is a deviation of 10 beats per minute (bpm) of the median heart rate bpm. In some embodiments, the predetermined percentage of measurements may be at least 90% of the total measured heart rate measurements. In some embodiments, the predefined value range may be a deviation of 10% of the median heart rate.

In some embodiments, the method may set the consistency threshold at the greater of (a) a first predefined value range, wherein the first predefined value range is equal to a range where 90% of the data falls within 10% deviation of a calculated mean of the heart data and (b) a second predefined value having no more than a deviation of 10 bpm from the calculated mean heart data. In some embodiments, the consistency threshold may be measured as a predetermined percentage of the measurements being within a predefined value range. In some embodiments, the method may include setting the consistency threshold as a range wherein an upper threshold of the range is established as a largest value of the heart data and a lower threshold of the range is established as a smallest value of the heart data.

In some embodiments, the method may include eliminating at least one channel from a heart rhythm analysis when the at least one channel does not satisfy the consistency threshold. In some embodiments, when at least two channels do not satisfy the consistency threshold, the method may identify one or more common electrodes present in the inconsistent channel.

In some embodiments, the method may include determining when the patient is experiencing an ambulatory period and examining the heart data during the ambulatory period. In some instances, the method analyzes a QRS width from the heart data for the predetermined time period. In at least one embodiment, the consistency threshold may be a deviation of 10% of the median QRS width. In some embodiments, the predetermined percentage of measurements may be at least 90% of the total measured heart rate measurements.

In some embodiments, the consistency threshold may be calculated for each channel of the at least three channels for the predetermined time period. In some embodiments, the method may include analyzing a QRS width and heart rate beats per minute data from the heart data for each of the at least three channels for the predetermined time period. In some embodiments, if no channel meets consistency criteria, then all channels will be used for a rhythm analysis.

In one embodiment, a WCD is described. The WCD includes a support structure wearable by a person and a processor coupled to the support structure. At least three sensing electrodes are in communication with the processor. A discharge circuit is configured to discharge a stored electrical charge through a body of the patient and is in communication with the processor. The processor is configured to connect to at least three sensing electrodes and obtain a signal from each of the at least three sensing electrodes. The processor is further configured to define at least three channels between the at least three electrodes and obtain heart data for a predetermined time period from the at least three channels wherein the heart data includes heart rate and QRS width. The processor also compares the heart data of each of the at least three channels to a consistency threshold.

In some embodiments, the processor may be further configured to determine when at least one of the at least three channels satisfies the consistency threshold and perform a rhythm analysis using the at least one channel that satisfies the consistency threshold. In some embodiments, the consistency threshold may be measured as a predetermined percentage of the measurements being within a predefined value range. In some embodiments, the predefined value range may be a deviation of 10 beats per minute (bpm) of the median heart rate bpm. In some embodiments, the predetermined percentage of measurements may be at least 90% of the total measured heart rate measurements.

In some embodiments, the predefined value range may be a deviation of 10% of the median heart rate. In some embodiments, the processor may be further configured to set the consistency threshold at the greater of (a) a first predefined value range, wherein the first predefined value range is equal to a range where 90% of the data falls within 10% deviation of a calculated mean of the heart data and (b) a second predefined value having no more than a deviation of 10 bpm from the calculated mean heart data. In some embodiments, the consistency threshold may be measured as a predetermined percentage of the measurements being within a predefined value range.

In some embodiments, the processor may be further configured to set the consistency threshold as a range wherein an upper threshold of the range is established as a largest value of the heart data and a lower threshold of the range is established as a smallest value of the heart data. In some embodiments, the processor may be further configured to eliminate at least one channel from a heart rhythm analysis when the at least one channel does not satisfy the consistency threshold. In some embodiments, when at least two channels do not satisfy the consistency threshold, the processor may be further configured to identify one or more common electrodes present in the inconsistent channel. In some embodiments, the processor may be further configured to analyze a QRS width from the heart data for the predetermined time period. In some embodiments, the consistency threshold may be a deviation of 10% of the median QRS width.

In some embodiments, the predetermined percentage of measurements may be at least 90% of the total measured heart rate measurements. In some embodiments, the consistency threshold may be calculated for each channel of the at least three channels for the predetermined time period. In some embodiments, the processor may be further configured to analyze a QRS width and heart rate beats per minute data from the heart data for each of the at least three channels for the predetermined time period. In some embodiments, if no channel meets consistency criteria, then the processor is further configured to use all channels for a rhythm analysis.

In one embodiment, a method to monitor a heart of a patient is described. The method includes connecting to at least three sensing electrodes and obtaining a signal from each of the at least three sensing electrodes. The method also includes defining at least three channels between the at least three electrodes obtaining heart data for a predetermined time period from the at least three channels wherein the heart data includes heart rate and QRS width. The method includes comparing the heart data of each of the at least three channels to a consistency threshold, wherein the consistency threshold is measured as a predetermined percentage of the measurements being within a predefined value range. The method further includes determining when at least one of the at least three channels satisfies the consistency threshold and performing a rhythm analysis using the at least one channel that satisfies the consistency threshold.

BRIEF DESCRIPTION OF THE DRAWINGS

The foregoing aspects and many of the attendant advantages of this disclosure will become more readily appreciated as the same becomes better understood by reference to the following detailed description, when taken in conjunction with the accompanying drawings, wherein.

DETAILED DESCRIPTION

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest and other potential heart conditions. Because WCDs are worn by ambulatory patients, noise on an ECG signal may be generated at the electrode-skin interface. For example, patient movement may cause movement at the electrode-skin interface to generate noise that may interfere with ECG interpretation. This noise may then interfere with obtaining accurate heart-rate signals, which may result in a missed cardiac episode.

In some embodiments, a WCD device may have four monitoring electrodes that can generate six differential ECG vectors. During patient movement, some ECG vectors may be noisier than other ECG vectors. As described herein, identifying more reliable ECG vectors for ECG characteristic assessment provides greater reliability.

In one embodiment, the history of each vector, or channel, is considered in the channel selection for the ECG characteristics assessment. This may include running multiple successive analyses on each channel. The channel or channels that produce a consistent result over time may be considered more reliable than a channel or channels that produce an inconsistent result over time.

In an ambulatory situation, one or more electrodes may be disturbed, and a motion artifact will appear in the associated ECG vectors or channels. However, other electrodes may not be disturbed during the ambulatory event such that the ECG channels with undisturbed electrodes may not have a motion artifact.

For exemplary purposes only, the embodiments herein will be described in reference to a WCD system and a defibrillator. However, the methodology for detecting and storing an arrhythmic episode can be performed by a WCD or any wearable medical monitoring device that monitors a patient's ECG.

Figure 1:
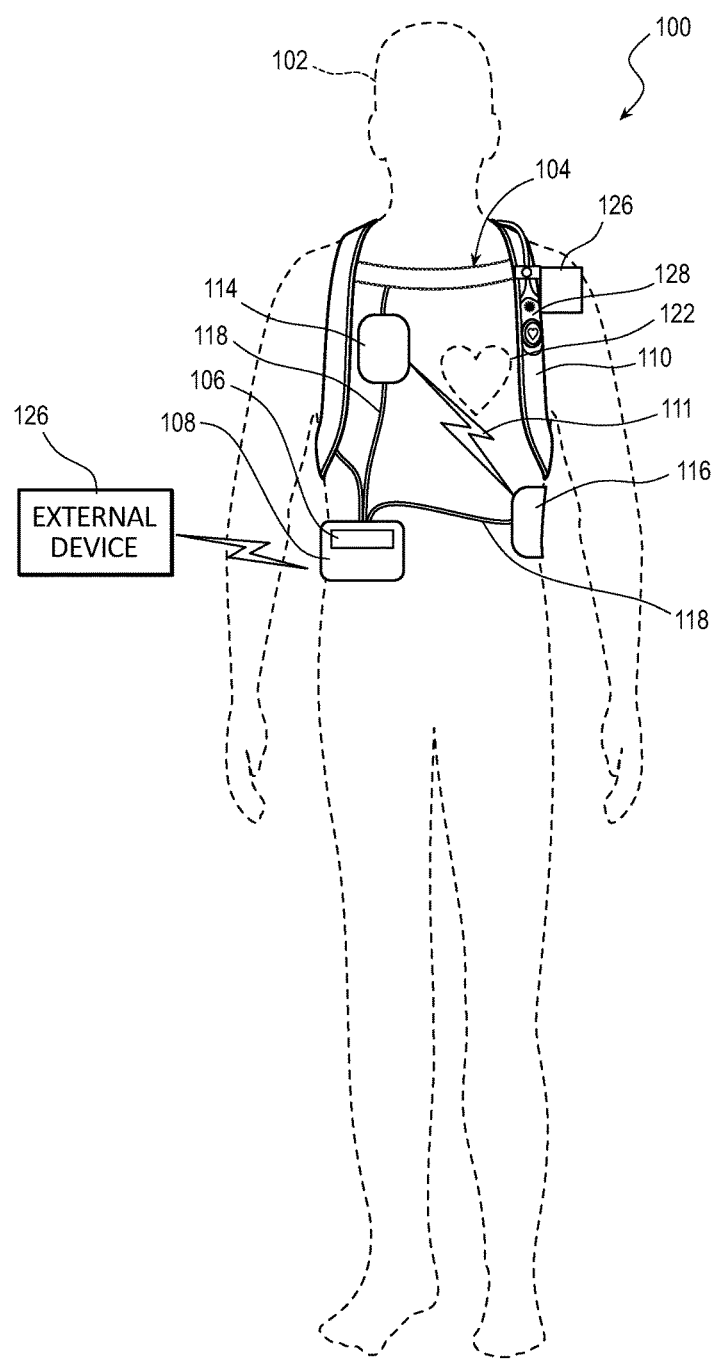
FIG. 1 is a diagram of a sample WCD system in accordance with exemplary embodiments described herein.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT), or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102, such as in a cart, bag, stroller, wheelchair, or another vehicle.

The external defibrillator 108 may be coupled to the support structure 110 or may be carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in a number of ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso 112 by being attached to the skin of patient 102, simply pressed against the skin directly or through garments, etc. In some embodiments, the electrodes 114, 116 are not necessarily pressed against the skin but become biased that way upon sensing a condition that could merit intervention by the WCD system 104. In addition, many of the components of defibrillator 108 can be considered coupled to support structure 110 directly or indirectly via at least one of the defibrillation electrodes 114, 116.

The WCD system 104 may defibrillate the patient 102 by delivering an electrical charge, pulse, or shock 111 to the patient 102 through a series of electrodes 114, 116 positioned on the torso 112. For example, when defibrillation electrodes 114, 116 are in good electrical contact with the torso 112 of patient 102, the defibrillator 108 can administer, via electrodes 114, 116, a brief, strong electric pulse 111 through the body. The pulse 111 is also known as shock, defibrillation shock, therapy, electrotherapy, therapy shock, etc. The pulse 111 is intended to go through and restart heart 122 in an effort to save the life of patient 102. The pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124, which may also be known as an outside monitoring device. The monitoring device 124 may monitor at least one local parameter. Local parameters may include a physical state of the patient 102, such as ECG, movement, heart rate, pulse, temperature, and the like. Local parameters may also include a parameter of the WCD 104, environmental parameters, or the like. The monitoring device 124 may be physically coupled to the support structure 110 or may be proximate to the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102 and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly as encompassing many individual sensors.

In some embodiments, a communication device 106 may enable the patient 102 to interact with and garnish data from the WCD system 104. The communication device 106 may enable a patient or third party to view patient data, dismiss a shock if the patient is still conscious, turn off an alarm, and otherwise engage with the WCD system 104. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient, and the WCD system 104 may include a separate communication device 106 remote from the defibrillator 108.

In some embodiments, the communication device 106 may be communicatively coupled to an alert button 128. The alert button 128 may be removably coupled to the support structure 110. The patient 102 may couple the alert button 128 to the support structure 110 or may couple the alert button 128 to an article of clothing. The alert button 128 may have a wired or wireless connection to the communication device 106. In some embodiments, the alert button 128 may include a visual output, an audio output, and a user input. The visual output may include a light, such as an LED, a small screen, or some combination thereof. Likewise, the audio output may include one or more speakers. The output of the audio output may be loud enough to be heard over nominal background noise. In some embodiments, the audio output might have an adjustable volume range. In some embodiments, the alert button 128 may include a microphone. In still further embodiments, the alert button 128 may also include a haptic response.

In some embodiments, the defibrillator 108 may connect with one or more external devices 126. For example, as shown in FIG. 1, the defibrillator 108 may connect to various external devices 126 such as the cloud, a remote desktop, a laptop, a mobile device, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include a number of aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system in order to make its diagnoses more accurate since patients' bodies differ from one another. Of course, such parameter values can be stored in a memory of the WCD system and the like. Moreover, a programming interface can be made according to embodiments, which receives such measured values of baseline physiological parameters. Such a programming interface may input automatically in the WCD system these, along with other data.

Figure 2:
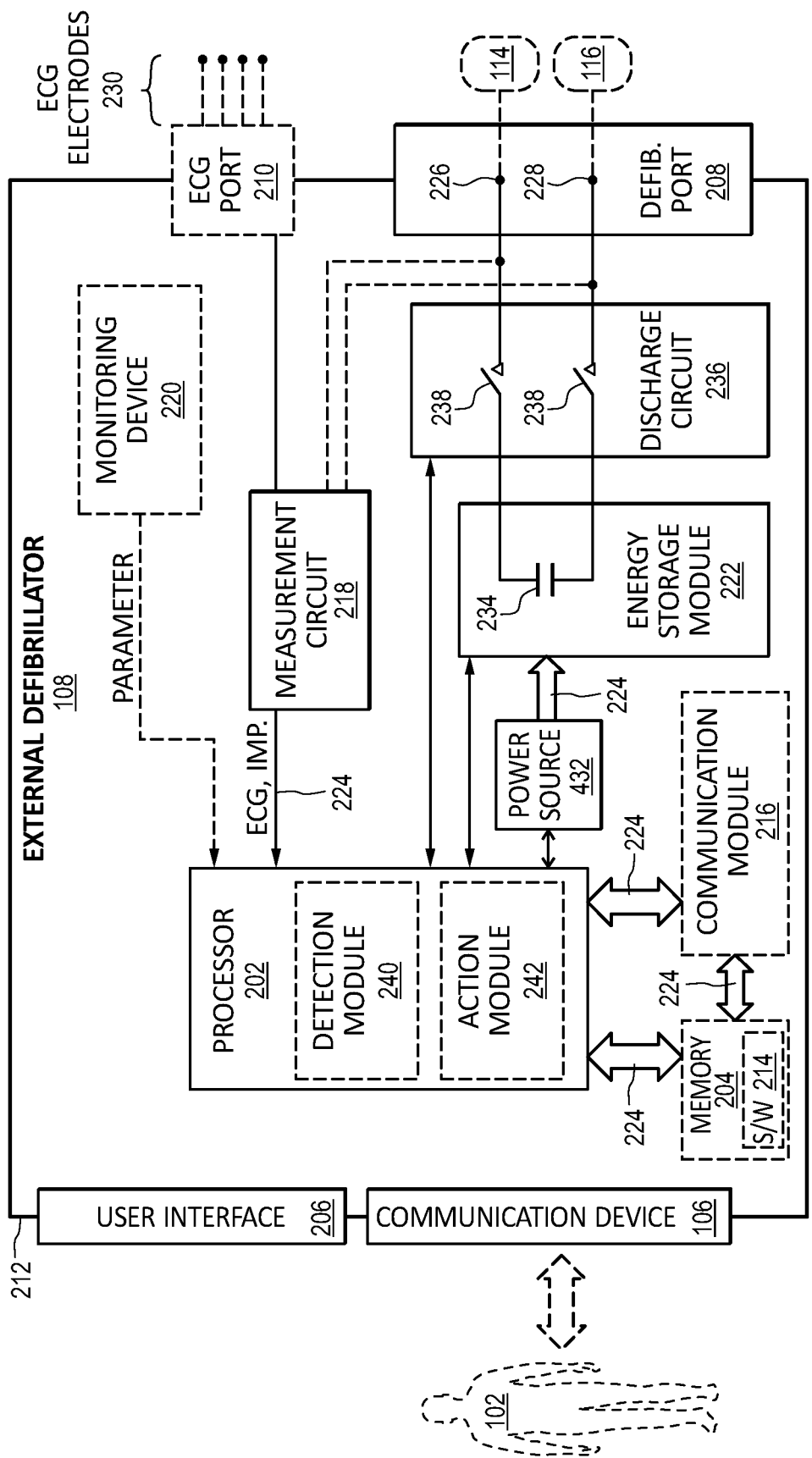
FIG. 2 is a block diagram of an example defibrillator in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read-only memory (ROM), flash RAM, and/or other types. The memory 204 may store computer-readable, computer-executable software/firmware code 214, including instructions that, when executed, cause the processor 202 to perform various functions (e.g., determine shock criteria, determine consciousness of patient, track patient parameters, establish electrode channels, determine noise levels in electrode readings, etc.). In some embodiments, the processor 202 may include an intelligent hardware device, e.g., a central processing unit (CPU), a microcontroller, an application-specific integrated circuit (ASIC), etc.

In some embodiments, the memory 204 can contain, among other things, the Basic Input-Output system (BIOS), which may control basic hardware and/or software operations such as interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 406 may be in addition to or part of the communication device 106. The user interface 406 may display an ECG of the patient, a status of the defibrillator 108, a status of a charge (e.g., a battery charge or an energy storage module), and the like.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g., defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g., leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 220 within the housing 212. The monitoring device 220 may monitor at least one local parameter. Local parameters may include the physical state of the patient, such as ECG, movement, heart rate, pulse, temperature, and the like. Local parameters may also include a parameter of the WCD system (e.g., WCD 104, FIG. 1), defibrillator 108, environmental parameters, or the like.

In some embodiments, the WCD system 104 may include an internal monitoring device 220 and an external monitoring device (e.g., external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate to an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy in preparation or anticipation of providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrically couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include one or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardware separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, and so on.

In some embodiments, the processor 202 may execute one or more modules. For example, the processor 202 may execute a detection module 240 and/or an action module 242. The detection module 240 may be a logic device or algorithm to determine if any or a variety of thresholds are exceeded, which may require an action from the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of battery power at the power source 232 or the energy storage module 222, or one or more electrodes (e.g., ECG electrodes, defibrillation electrodes) may have lost connection. In such instances, the action module 242 may trigger an alert to the patient or to an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
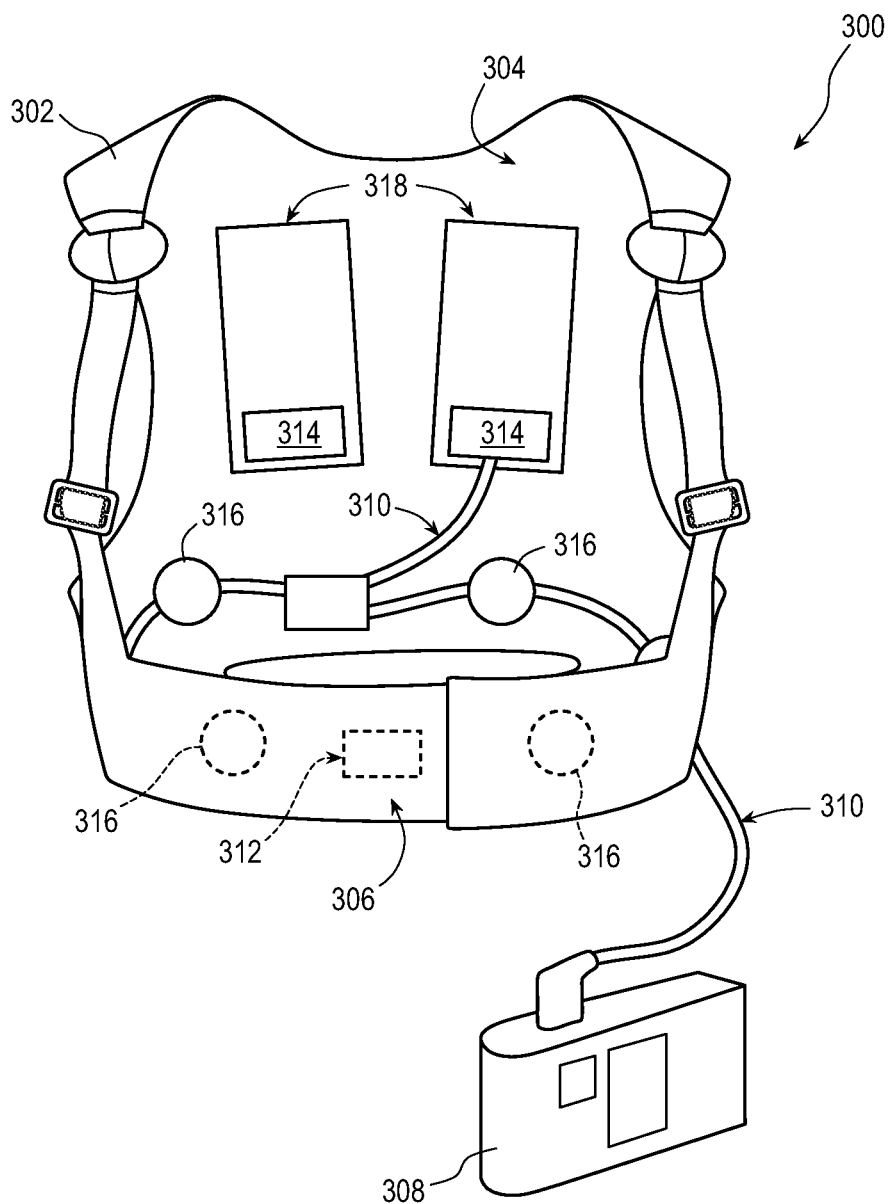
FIG. 3 is a diagram of sample embodiments of components of a WCD system in accordance with exemplary embodiments described herein.

FIG. 3 is a diagram of sample embodiments of components of a WCD system 300 according to exemplary embodiments. The WCD system 300 may be an example of the WCD system 104 described with reference to FIG. 1. In some embodiments, the WCD system 300 may include a support structure 302 comprising a vest-like wearable garment. In some embodiments, the support structure 302 has a backside 304 and a frontside 306 that closes in front of the chest of the patient.

In some embodiments, the WCD system 300 may also include an external defibrillator 308. The external defibrillator 308 may be an example of the defibrillator 108 described with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of pockets 318 may comprise loose netting so that the electrodes 314 can contact the back of the patient. In some instances, a conductive fluid may be deployed to increase connectivity. Additionally, in some embodiments, sensing electrodes 316 are maintained in positions that surround the patient's torso for sensing ECG signals and/or the impedance of the patient.

In some instances, the ECG signals in a WCD system 300 may comprise too much electrical noise to be useful. To ameliorate the noise problem, multiple ECG sensing electrodes 316 are provided for presenting many options to the processor (e.g., processor 202, FIG. 2). The multiple ECG sensing electrodes 316 provide different vectors for sensing the ECG signal of the patient.

Figure 4:
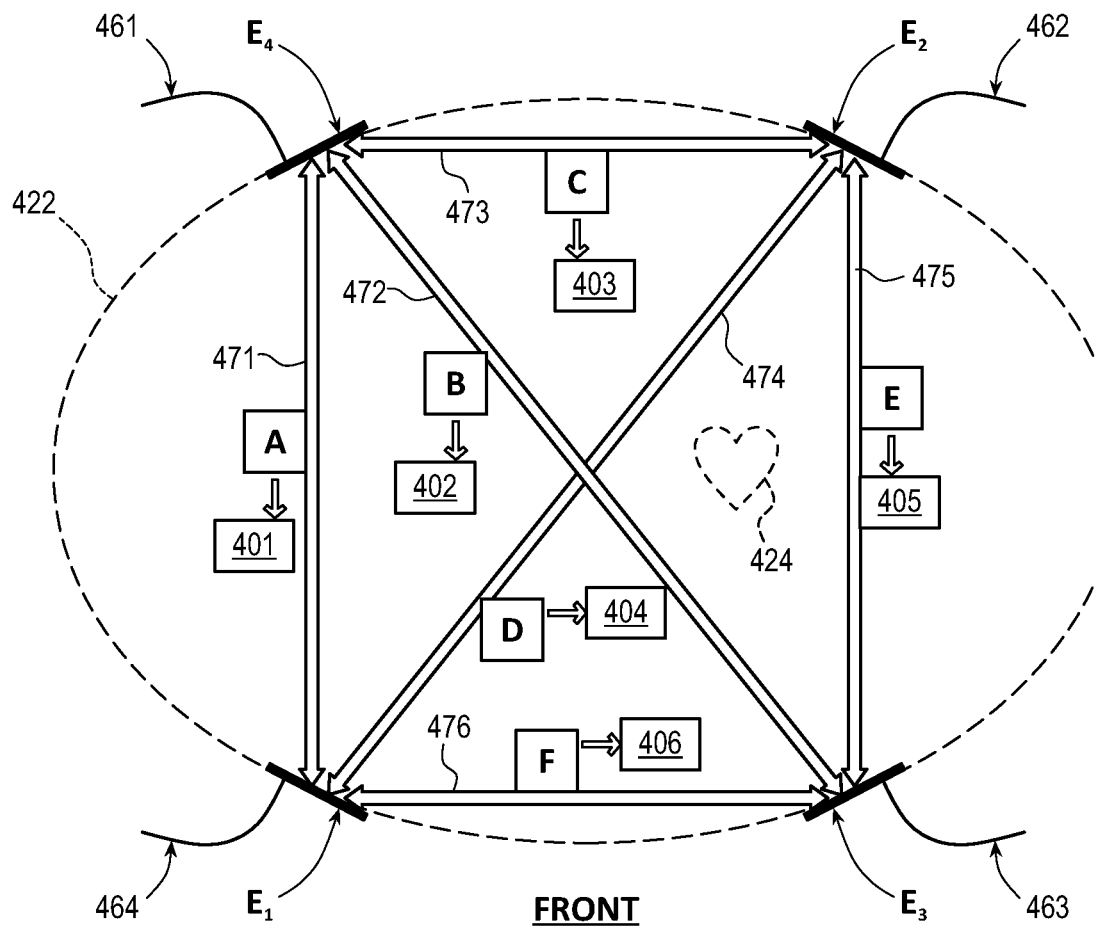
FIG. 4 is a conceptual diagram illustrating multiple electrodes of a WCD system in accordance with exemplary embodiments described herein.

FIG. 4 is a conceptual diagram illustrating how multiple electrodes of a WCD system may define a multi-vector embodiment for sensing ECG signals along different vectors according to various exemplary embodiments. A cross-section of a body of a patient 422 having a heart 424 is illustrated. In FIG. 4, the patient 422 is viewed from the top looking down, and the plane of FIG. 4 intersects patient 422 proximate the torso of the patient 422.

In some embodiments, four ECG sensing electrodes $E_1$, $E_2$, $E_3$, $E_4$ are maintained on the torso of patient 482 and have respective wire leads 461, 462, 463, 464. The electrodes $E_1$, $E_2$, $E_3$, $E_4$ that surround the torso may be similar to the sensing electrodes 316 as described with reference to FIG. 3.

Any pair of these four ECG sensing electrodes $E_1$, $E_2$, $E_3$, $E_4$ defines a vector along which an ECG signal may be sensed and, in some instances, measured. As such, electrodes $E_1$, $E_2$, $E_3$, $E_4$ define six vectors 471, 472, 473, 474, 475, 476.

These vectors 471, 472, 473, 474, 475, 476 define channels A, B, C, D, E, F, respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

As shown in FIG. 4, electrodes $E_1$, $E_2$, $E_3$, $E_4$ are drawn on the same plane for simplicity, while in actuality, the electrodes $E_1$, $E_2$, $E_3$, $E_4$ may not be positioned on the same plane. Accordingly, vectors 471, 472, 473, 474, 475, 476 are not necessarily on the same plane, either. Further, in some embodiments, the WCD system averages a value of the voltages of all four electrodes electronically and then determines the voltage of each electrode relative to the average value. Conceptually, this average value is the signal at some point in space in between the electrodes $E_1$, $E_2$, $E_3$, $E_4$. It continuously changes its virtual position based on the voltages of the electrodes $E_1$, $E_2$, $E_3$, $E_4$. In some embodiments, this virtual point is referred to herein as the M Central Terminal (MCT). Relative to the MCT, there are four resulting vectors: E1C=E1−CM, E2C=E2−CM, E3C=E3−CM and E4C=E4−CM, where CM is the average voltage value. In some embodiments, the vectors are virtually formed by selecting a pair of these signals and subtracting one from the other. For example, E1C−E2C=(E1−CM)−(E2−CM)=E1−E2+(CM−CM)=E1−E2=E12. Although six vectors are described in FIG. 4, a different number of vectors may be used depending on the number of ECG electrodes present in the system and the desired number of vectors (up to the number of vectors that can be derived from the number of electrodes).

In some embodiments, to make the shock/no-shock determination as accurate as possible, a WCD system may assess the best ECG signals 401, 402, 403, 404, 405, 406 for rhythm analysis and interpretation. For example, ECG signals with the most noise may be ignored, discarded, or not considered, leaving the remaining ECG signals as candidates for the shock/no-shock determination.

In other embodiments, the vectors may be aggregated to make a shock/no-shock decision and/or to determine the patient's heart rate and/or QRS widths. For example, in some embodiments, the aggregation can be implemented as disclosed in U.S. Pat. No. 9,757,581 issued Sep. 12, 2017, entitled "Wearable Cardioverter Defibrillator Components Making Aggregate Shock/No Shock Determination from Two or More ECG Signals," which is incorporated herein by reference.

Figure 5:
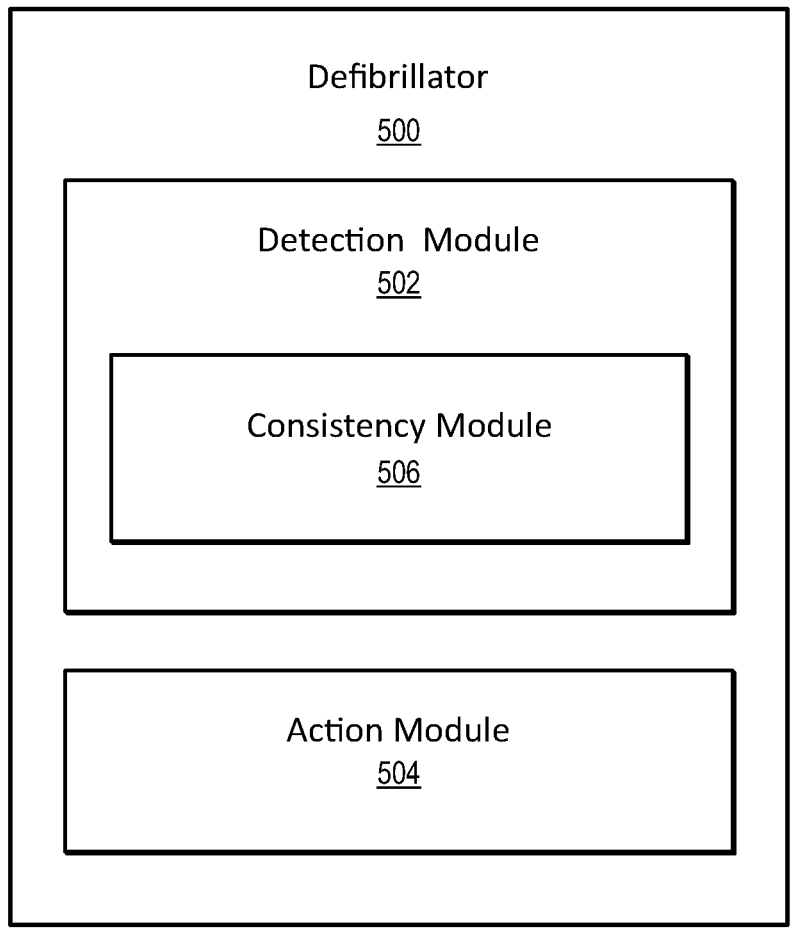
FIG. 5 is a is a block diagram of an example defibrillator in accordance with exemplary embodiments described herein.

FIG. 5 is a block diagram illustrating components of one example of a defibrillator 500. The defibrillator 500 may be an example of the defibrillator 108 described with reference to FIGS. 1 and 2 and defibrillator 308 described with reference to FIG. 3. In this example, the defibrillator 500 has detection module 502 and an alert module 504. The detection module 502 may further include a consistency module 506.

In some embodiments, the consistency module 506 may review the history of each channel for an ECG characteristic assessment. In some embodiments, the consistency module 506 may run multiple successive analyses on each channel. The consistency module 506 may consider channels that produce a consistent result over time to be more reliable than other channels that produce an inconsistent result over time.

Figure 6:
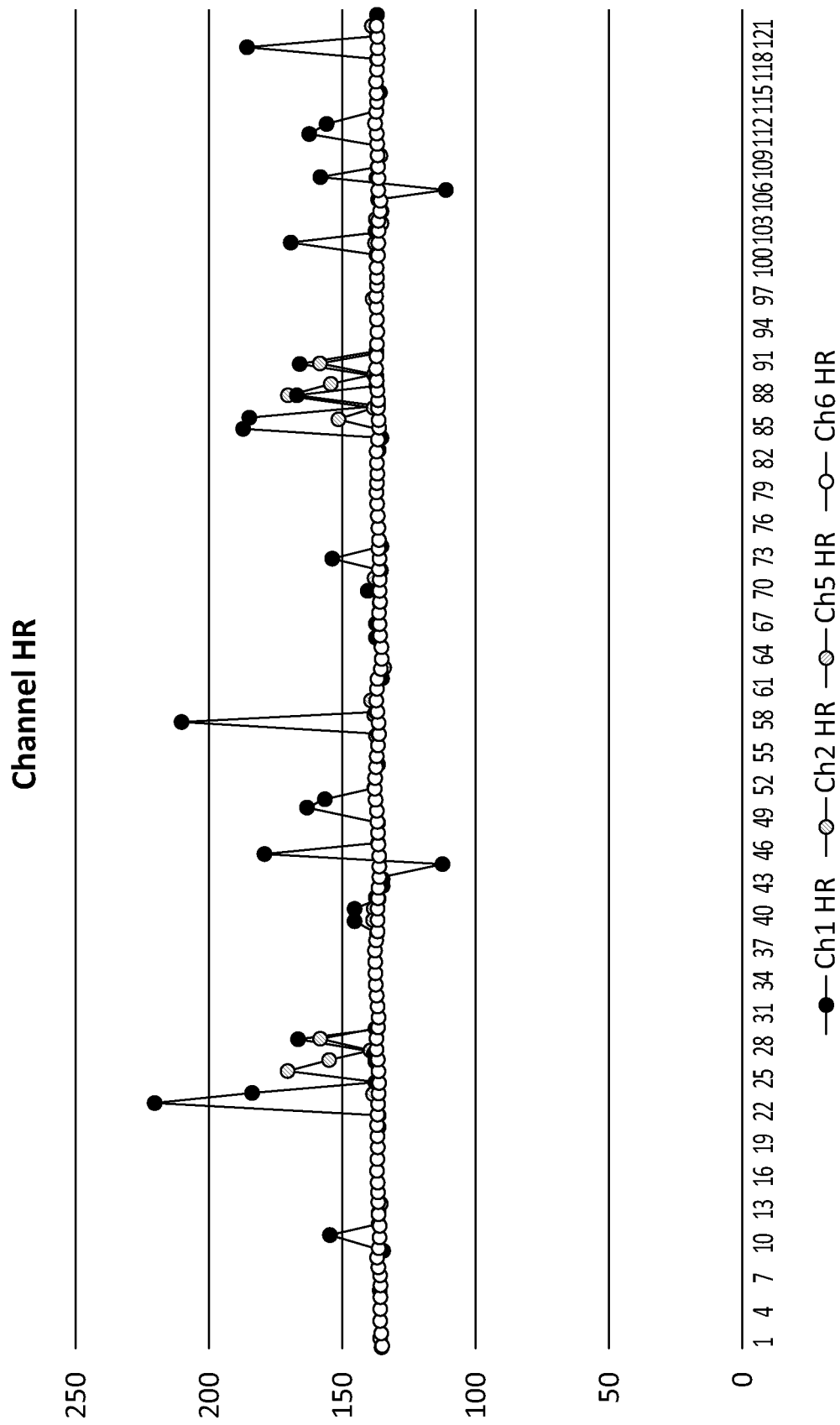
FIG. 6 illustrates an exemplary heart rate data graph for a predetermined time period in accordance with exemplary embodiments described herein.

As shown in FIG. 6, the consistency module 506 may plot out each individual channel as measured during an ambulatory period for the corresponding ECG vectors. In the example shown, only four channels are graphically represented: channel 1 as shown by the solid dot with a connecting line; channel 2 as shown by the right slanting crosshatch dot with a connecting line; channel 5 as shown by the left-slanting crosshatch dot with a connecting line; and channel 6 shown as the clear dot with a connecting line. The example shown in FIG. 6 is for an exemplary ambulatory period. As can be seen in FIG. 6, channel 5 and channel 6 show a consistent heart rate reading of around 140 beats per second (bps). Channel 5 may be blocked by channel 6.

In contrast, as shown in the example in FIG. 6, channel 1 and channel 2 show a disturbed heart rate due to a motion artifact from electrode 1. Electrode 1 must have been jostled or otherwise become dislodged or catawampus. The inconsistent heart rate can be seen by the large peaks and variations in FIG. 6. Therefore, for the exemplary time period shown, the consistency module 506 may disregard the readings from channel 1 and channel 2 due to their inconsistencies.

Referring back to FIG. 5, in some embodiments, the consistency module 506 may estimate the consistency of a channel over a time period of interest. The time period of interest may be between thirty (30) seconds and two (2) minutes. In some embodiments, the consistency module 506 may have a set predetermined time period. In other embodiments, the time period may change based on the current conditions. Conditions that may impact the time duration may include the ambulatory length of time, a suspected cardiac event, and the like. In some embodiments, the consistency module 506 may begin by examining a thirty-second stretch of data. If the data is inconclusive, the consistency module 506 may lengthen the time period. If the consistency module 506 cannot find any consistent history even with a longer time period being inspected, the consistency module 506 may continue with the heart rate analysis and issue an alert to troubleshoot potential noise-causing issues.

Consistent data may be defined as a percentage of the heart rate measurements as being within a predefined value range. In some embodiments, the predefined value range may be plus or minus ten bpm (+/−10 bpm). In other embodiments, the consistency module 506 may use a predefined percentage range of plus or minus ten percent (+/−10%) of the median heart rate or another type of average heart rate during the time period of interest. As mentioned previously, the time range of interest may be the preceding thirty (30) to one hundred twenty (120) seconds of the ECG signal. For example, the time range may be a closely preceding time period, such as 30-120 seconds. In some embodiments, both the value range and the percentage range may be calculated. In further embodiments, where both the value range and percentage range are calculated, the consistency module 506 may use the larger value for the range of a "consistent" channel.

In some embodiments, the consistency module 506 may estimate the consistency of a heart rate as a standard deviation or variance of incoming heart rate values in the predetermined time period of interest. The consistency module 506 may then compare the standard deviation to a threshold defining consistent versus inconsistent heart rate data.

In some embodiments, the consistency module 506 may define a heart rate range. The heart rate range may be calculated by subtracting the smallest value from the largest value without considering the median. Once the range is determined for the predetermined time period, the consistency module 506 may compare the range to a threshold for defining consistent versus inconsistent channels.

Referring back to FIG. 6, in some embodiments, the consistency threshold may eliminate channel 1 from further analysis. In other embodiments, depending on how the threshold is set, the data from channel 1 may fall within the threshold. In still further embodiments, the consistency threshold may eliminate channel 1 and channel 2 when the consistency threshold is more stringent. In some embodiments, if no channel meets the consistency threshold, then the consistency module 506 may assume a real cardiac event is occurring and use all channels for the rhythm analysis.

Figure 7:
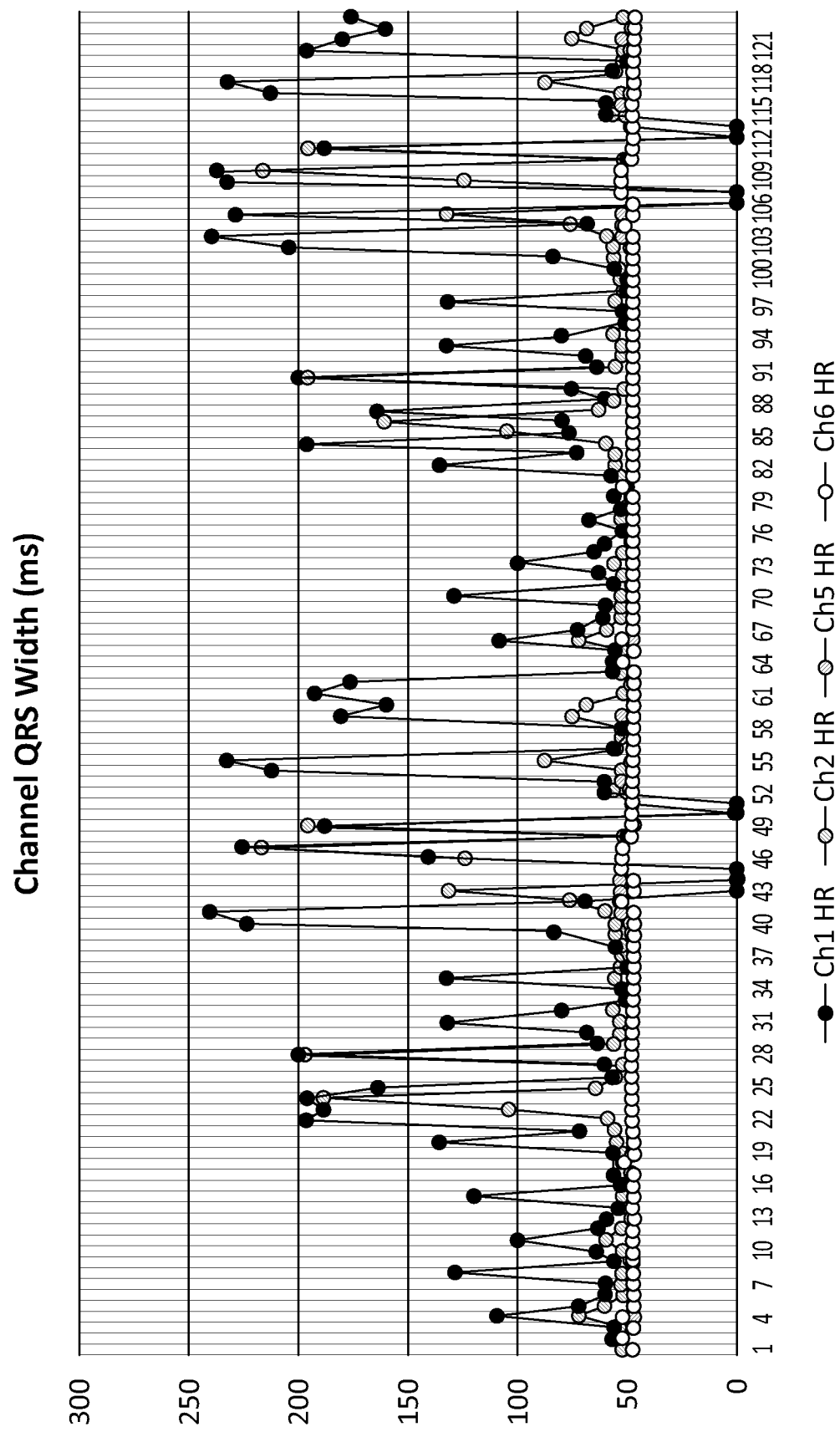
FIG. 7 illustrates an exemplary QRS width data graph for a predetermined time period in accordance with exemplary embodiments described herein.

Referring back to FIG. 5, in some embodiments, the consistency module 506 may analyze the QRS width history in addition to the heart rate data or as an alternative to the heart rate data. As shown in FIG. 7, the consistency module 506 may plot out the QRS width for each individual channel as measured during an ambulatory period for the corresponding ECG vectors. In the example shown, only four channels are graphically represented: channel 1 as shown by the solid dot with a connecting line; channel 2 as shown by the right slanting crosshatch dot with a connecting line; channel 5 as shown by the left-slanting crosshatch dot with a connecting line; and channel 6 shown as the clear dot with a connecting line. In the example shown, channel 5 and channel 6 display a consistent QRS width, whereas channel 1 and channel 2 show a disturbed QRS width due to a motion artifact from electrode 1. Similar to the heart rate example discussed previously, in some embodiments, the consistency module 506 may dismiss the QRS widths of channel 1 during this ambulatory period in a rhythm analysis. In further embodiments, the consistency module 506 may dismiss channel 1 and channel 2 in a rhythm analysis.

Again, consistent data may be defined as a percentage of the heart rate measurements as being within a predefined value range when measured by QRS widths. In some embodiments, the predefined value range may be plus or minus ten ms (+/−10 ms). In other embodiments, the consistency module 506 may use a predefined percentage range of plus or minus ten percent (+/−10%) of the median QRS. As mentioned previously, the time range of interest may be the preceding thirty (30) to one hundred twenty (120) seconds of the ECG signal. For example, the time range may be a closely preceding time period, such as 30-120 seconds. In some embodiments, both the value range and the percentage range may be calculated. In further embodiments, where both the value range and percentage range are calculated, the consistency module 506 may use the larger value for the range of a "consistent" channel.

Referring back to FIG. 5, in some embodiments, for rhythm analysis, the consistency module 506 may use either or both the heart rates and QRS widths of channels or segments that satisfy the consistency threshold. For example, in some embodiments, the consistency module 506 may process the heart rates, QRS widths, or some combination thereof of the channels or time segments as a mathematical combination. In some embodiments, the mathematical combination may be the median value of the heart rates, QRS widths, or some combination thereof. In some embodiments, the consistency module 506 may use an average instead of the median value.

In some embodiments, the consistency module 506 may estimate or assign a consistency rating for each channel. The consistency module 506 may then use assigned consistency ratings to calculate a weighted average or the heart rate, QRS widths, or some combination thereof. The weighted average may include all available channels or a specific combination of channels. For example, the consistency module 506 may only use channels that satisfy a consistency threshold for either HR or QRS width. In some embodiments, the consistency module 506 may only use a subset of channels regardless of a consistency threshold. For example, the consistency module 506 may use the most consistent three channels. The consistency module 506 may determine the most consistent channels by determining which channels have the least variation in data. In still further embodiments, the consistency module 506 may only use the channels that meet the desired consistency rating. This may mean the consistency module 506 uses only one channel.

If the consistency module 506 fails to identify any channels that meet a minimum consistency threshold, the consistency module 506 may alert the action module 504 and then continue to analyze the channels with new sets of data to determine if the consistency of the channels change over time. In further embodiments, if no channel meets the consistency threshold, then the consistency module 506 may assume a real cardiac event is occurring and use all channels for the rhythm analysis.

In some embodiments, the consistency module 506 may track inconsistent channels. For example, the consistency module 506 may record every time a channel has an inconsistent rating and may also record the electrodes that are the likely culprit of the inconsistency. This data may determine that the patient continuously has a problem with a specific electrode during their ambulatory periods. In still further embodiments, the consistency module 506 may also be able to track the inconsistent channel times with specific exercises or activities the patient is performing at that time. This may enable the detection module 502 and action module 504 to alert the patient to be aware of a potential electrode issue when a specific activity begins. In some embodiments, the activity itself might not spark a problem with a specific electrode but may ignite a consistent channel every time the action is undertaken. Therefore, the alert may simply have the patient troubleshoot all electrodes at the end of the activity.

The action module 504 may use channels identified by the consistency module 506 to make a shock/no-shock decision. The action module 504 may analyze the heart rate and QRS data from the consistent channels to determine if the patient is having a cardiac event.

At the same time, in some embodiments, the action module 504 may alert the patient of a potential electrode connectivity issue based at least in part on the inconsistent channels. For example, the consistency module 506 may ascertain common electrodes in inconsistent channels and pass this information on to the action module 504. The action module 504 may then cause an alert to be issued to the patient to troubleshoot the issue.

The action module 504 may also use a combination of heart rate and QRS widths to make shock/no-shock decisions. The action module 504 may use methods similar to those disclosed in U.S. Pat. No. 10,016,614 entitled "Wearable Cardioverter Defibrillator (WCD) System Making Shock/No Shock Determinations by Aggregating Aspects of Multiple Patient Parameters" or U.S. Pat. No. 10,105,547 entitled "Wearable Cardioverter Defibrillator (WCD) Causing Patient's WRS Width to be Plotted Against the Heart Rate," both of which are incorporated by reference herein.

Figure 8:
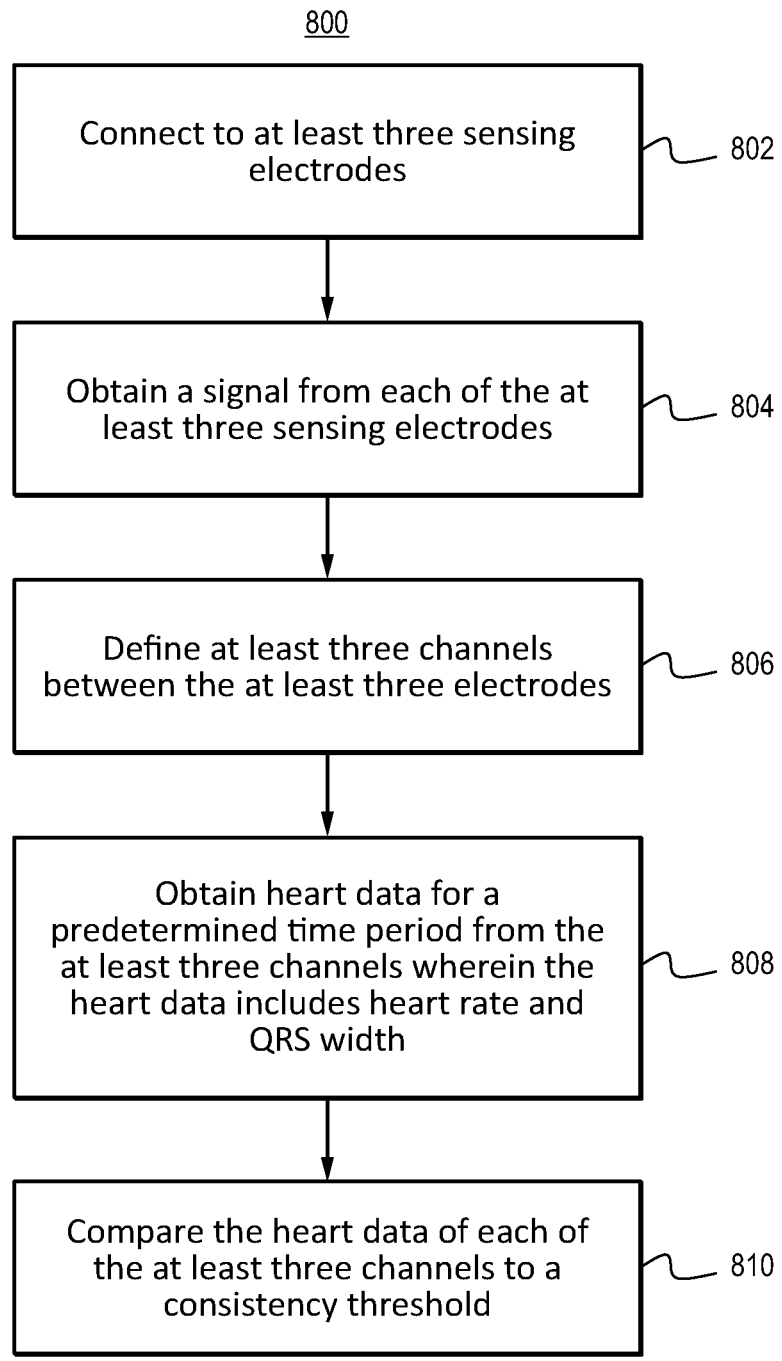
FIG. 8 is an exemplary flow diagram in accordance with exemplary embodiments described herein.

FIG. 8 is a flow chart illustrating an example of a method 800 for WCD systems, in accordance with various aspects of the present disclosure. For clarity, the method 800 is described below with reference to aspects of one or more of the systems described herein.

At block 802, the method 800 may connect to at least three sensing electrodes. The sensing electrodes may be coupled to or somehow attached to a patient in such a way that the electrodes may sense a heart signal from the patient. At block 804, the method 800 may obtain a signal from each of the at least three sensing electrodes. Next, at block 806, the method 800 may define at least three channels between the at least three electrodes.

At block 808, the method 800 may obtain heart data for a predetermined time period from the at least three channels. The heart data may include heart rate and QRS width. The predetermined time period may be a snapshot of an ambulatory period for the patient. In some embodiments, the predetermined time period may be between thirty (30) seconds and two (2) minutes.

At block 810, the method 800 may compare the heart data of the at least three channels to a consistency threshold. The consistency threshold may be defined as a percentage of the heart rate measurements as being within a predefined value range or a predefined percentage range of the median heart rate in the time period of interest. In some embodiments, setting the consistency threshold may include calculating both the value range and the percentage range and choosing the larger value for the consistency threshold.

Thus, the method 800 may provide for determining reliable ECG signals. It should be noted that the method 800 is just one implementation and that the operations of the method 800 may be rearranged or otherwise modified such that other implementations are possible.

Figure 9:
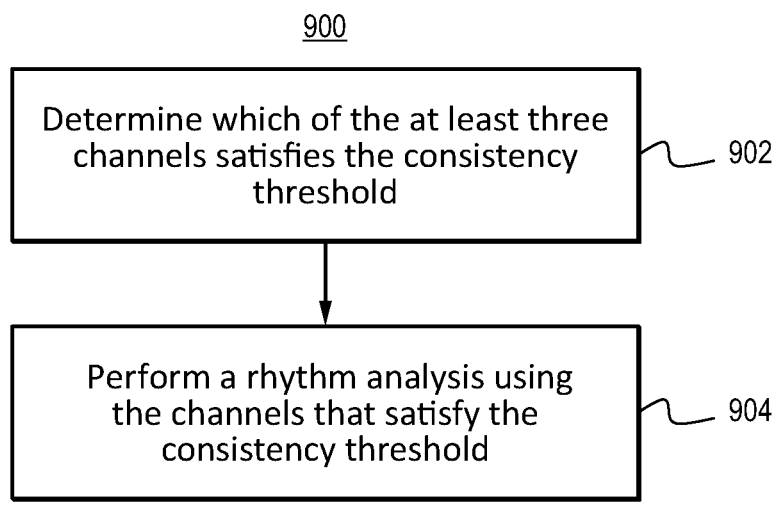
FIG. 9 is another exemplary flow diagram in accordance with exemplary embodiments described herein.

FIG. 9 is a flow chart illustrating an example of a method 900 for WCD systems, in accordance with various aspects of the present disclosure. For clarity, the method 900 is described below with reference to aspects of one or more of the systems described herein.

At block 902, the method 900 may decide which of the at least three channels satisfy the consistency threshold. For example, once the consistency threshold is set, the method 900 may compare the heart rate measurements to the threshold and determine if the channel has a consistent signal. As mentioned previously, the consistency threshold may be a percentage range such as plus or minus 10% of the median heart rate. In other embodiments, the consistency threshold may be a predefined value range, for example, plus or minus 10 bpm of the median heart rate.

Additionally, or alternatively, the consistency threshold may also be defined by a predefined value range of QRS width. For example, as mentioned previously, the consistency threshold may be a percentage range such as plus or minus 10% of the median QRS width. In other embodiments, the consistency threshold may be a predefined value range, for example, plus or minus 10 ms of the median QRS width.

Once the method 900 determines the consistency threshold and the channels that satisfy the threshold, then at block 904, the method 900 may perform a rhythm analysis using the channels that do satisfy the threshold. For example, if the channel or heart rate measurements are inconsistent and unreliable because an electrode came loose during an ambulatory period, that channel will have noise in the signal. The noise can cause faulty analysis and may misdiagnose a patient. The misdiagnosis can be problematic both ways. For example, it would be problematic to miss a cardiac event and not deliver the treatment the patient needed. It would also be problematic to wrongly diagnose a cardiac event and deliver treatment the patient did not need. Therefore, analyzing ECG signals to filter out noise helps to ensure accurate rhythm analysis. The consistency threshold helps determine which channels provide a consistent and steady ECG signal that is reliable.

Thus, the method 900 may provide for determining reliable ECG signals. It should be noted that the method 900 is just one implementation and that the operations of the method 900 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described in order to not unnecessarily obscure this description.

Some technologies or techniques described in this document may be known. Even then, however, it is not known to apply such technologies or techniques as described in this document or for the purposes described in this document.

This description includes one or more examples, but this fact does not limit how the invention may be practiced. Indeed, examples, instances, versions, or embodiments of the invention may be practiced according to what is described, or yet differently, and also in conjunction with other present or future technologies. Other such embodiments include combinations and sub-combinations of features described herein, including, for example, embodiments that are equivalent to the following: providing or applying a feature in a different order than in a described embodiment; extracting an individual feature from one embodiment and inserting such feature into another embodiment; removing one or more features from an embodiment, or both removing a feature from an embodiment and adding a feature extracted from another embodiment while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to," "adapted to," and/or "configured to" denote one or more actual states of construction, adaptation, and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description, a single reference numeral may be used consistently to denote a single item, aspect, component, or process. Moreover, a further effort may have been made in the preparation of this description to use similar though not identical reference numerals to denote other versions or embodiments of an item, aspect, component, or process that are identical or at least similar or related. Where made, such a further effort was not required but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component, or process rather than its reference numeral. Any similarity in reference numerals may be used to infer a similarity in the text, but not to confuse aspects where the text or other context indicates otherwise.

The claims of this document define certain combinations and subcombinations of elements, features, and acts or operations, which are regarded as novel and non-obvious. The claims also include elements, features, and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method to detect noise levels in electrocardiogram (ECG) signals, the method comprising:
   obtaining a signal from each of the at least three sensing electrodes;
   defining at least three channels between the at least three electrodes;
   determining heart data for a predetermined time period from the signals of the at least three channels wherein the heart data includes heart rate and QRS width; and
   comparing the heart data of each of the at least three channels to a consistency threshold, wherein the consistency threshold is measured as a predetermined percentage of the measurements being within a predefined value range.

2. The method of claim 1, further comprising:
   determining when at least one of the at least three channels satisfies the consistency threshold; and
   performing a rhythm analysis using the at least one channel that satisfies the consistency threshold.

3. The method of claim 1, wherein the predefined value range is a deviation of 10 beats per minute (bpm) of the median heart rate bpm.

4. The method of claim 1, wherein the predetermined percentage of measurements is at least 90% of the total measured heart rate measurements.

5. The method of claim 1, wherein the predefined value range is a deviation of 10% of the median heart rate.

6. The method of claim 1, further comprising:
   setting the consistency threshold at the greater of (a) a first predefined value range, wherein the first predefined value range is equal to a range where 90% of the data falls within 10% deviation of a calculated mean of the heart data and (b) a second predefined value having no more than a deviation of 10 bpm from the calculated mean heart data.

7. The method of claim 1, further comprising:
setting the consistency threshold as a range wherein an upper threshold of the range is established as a largest value of the heart data and a lower threshold of the range is established as a smallest value of the heart data.

8. The method of claim 1, further comprising:
eliminating at least one channel from a heart rhythm analysis when the at least one channel does not satisfy the consistency threshold.

9. The method of claim 8, wherein when at least two channels do not satisfy the consistency threshold, the method further comprising:
identifying one or more common electrodes present in the inconsistent channel.

10. The method of claim 1, further comprising:
analyzing a QRS width from the heart data for the predetermined time period; and
determining a median QRS width from the analyzed data.

11. The method of claim 10, wherein the consistency threshold is a deviation of 10% of the median QRS width.

12. The method of claim 1, wherein the predefined value range is a deviation of 10 milliseconds (ms) of the median QRS width.

13. The method of claim 1, further comprising:
setting the consistency threshold at the greater of (a) a first predefined value range, wherein the first predefined value range is equal to a range where 90% of the data falls within 10% deviation of a calculated mean of the heart data and (b) a second predefined value having no more than a deviation of 10 ms from the calculated mean heart data.

14. The method of claim 1, wherein the consistency threshold is calculated for each channel of the at least three channels for the predetermined time period.

15. The method of claim 1, further comprising:
analyzing a QRS width and heart rate beats per minute data from the heart data for each of the at least three channels for the predetermined time period.

16. The method of claim 1, further comprising:
determining when none of the at least three channels satisfies the consistency threshold; and
performing a rhythm analysis using all of the at least three channels.

17. The method of claim 2, further comprising providing therapy to the patient based on the rhythm analysis.

18. A method to monitor a heart of a patient, the method comprising:
connecting to at least three sensing electrodes;
obtaining a signal from each of the at least three sensing electrodes;
defining at least three channels between the at least three electrodes;
obtaining heart data for a predetermined time period from the at least three channels wherein the heart data includes heart rate and QRS width;
comparing the heart data of each of the at least three channels to a consistency threshold, wherein the consistency threshold is measured as a predetermined percentage of the measurements being within a predefined value range;
determining when at least one of the at least three channels satisfies the consistency threshold; and
performing a rhythm analysis using the at least one channel that satisfies the consistency threshold.

19. The method of claim 18, wherein the predefined value range is a deviation of 10 beats per minute (bpm) of the median heart rate bpm.

20. The method of claim 18, further comprising providing therapy to the patient based on the rhythm analysis.

* * * * *